United States Patent [19]

Illuminati et al.

[11] 4,163,861

[45] Aug. 7, 1979

[54] PROCESS FOR THE PREPARATION OF AROMATIC URETHANES

[75] Inventors: Gabriello Illuminati, Rome; Ugo Romano, Milan, both of Italy

[73] Assignee: Snamprogetti S.p.A., Milan, Italy

[21] Appl. No.: 851,739

[22] Filed: Nov. 15, 1977

Related U.S. Application Data

[63] Continuation of Ser. No. 589,898, Jun. 24, 1975, abandoned.

[51] Int. Cl.$^2$ ............................................. C07C 67/08
[52] U.S. Cl. .................................. 560/132; 560/134; 560/163
[58] Field of Search .................. 560/132, 163, 134

[56] References Cited

U.S. PATENT DOCUMENTS

| | | | |
|---|---|---|---|
| 2,822,348 | 2/1958 | Haslam | 560/103 |
| 2,834,799 | 3/1958 | Sowa | 560/157 |
| 3,404,208 | 10/1968 | Robertson et al. | 560/132 |
| 3,872,161 | 3/1975 | Fukuchi et al. | 560/217 |

OTHER PUBLICATIONS

Ohno Koji, Japan 74 16,275, Apr. 1974. (See Chemical Abstracts, vol. 82, (1975), No. 17,510g.

Kraft, William M., "The Preparation of Indanone by a Carbamate-Aldehyde Reaction," Journal of the American Chemical Society, 70, (1948), p. 3570.

Kirk-Othmer "Encyclopedia of Chemical Technology" vol. 14, p. 473, Interscience Publ. 1st Ed. (1955).

*Primary Examiner*—Bernard Helfin
*Assistant Examiner*—L. Hendriksen
*Attorney, Agent, or Firm*—Morgan, Finnegan, Pine, Foley & Lee

[57] ABSTRACT

An aromatic urethane (e.g., methyl naphthyl urethane) is prepared by reacting an aromatic hydroxy compound, such as alpha-naphthol, with an aliphatic urethane, such as dimethyl urethane, in the presence of a catalyst consisting of a Lewis acid.

4 Claims, No Drawings

PROCESS FOR THE PREPARATION OF AROMATIC URETHANES

This is a continuation of application Ser. No. 589,898, filed June 24, 1975 now abandoned.

The present invention relates to a process for the preparation of aromatic urethanes having the formula

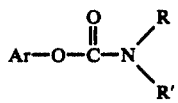

wherein Ar is an aromatic group of phenyl or naphthyl type, possibly containing substituents such as alkyl, alkoxy, aryl, aryl-oxy; R and R', the same or different, are alkyl radicals or hydrogen.

It is known that said compounds are synthetized from the respective phenol and alkyl isocyanates or from aryl-chloroformiates and amines by using a complex technology which entails considerable risks due to the toxicity of the reagents employed.

It is also known that said products have wide industrial applications as insecticides, some of which are particularly interesting because they have a low mammalian toxicity.

It has now been found that said compounds may be obtained by reacting aromatic hydroxy-compounds and aliphatic urethanes in the presence of suitable catalysts. The reaction is carried out in the liquid phase with or without solvent at temperatures between 100° and 300° C. and in particular between 150° and 250° C. The molar ratio between phenol and urethane is varied between 10:1 and 1:10. The compounds known as Lewis' acids, such as $AlX_3$ $TiX_4$ $FeX_3$ $ZnX_2$ $SnX_4$ (where X is halogen, alkoxy, aryl-oxy) are effective as catalysts.

As an illustration, not limitative, some examples of the above described reaction are given.

EXAMPLE 1

At 160° C. and 100 mm Hg, 14 g of alpha-naphthal and 9 g of dimethyl urethane were reacted in presence of 0.7 g of anhydrous $AlCl_3$. The reaction was continued for 6 hours, removing the methanol formed during the reaction. A 28% conversion of naphthal was obtained, with practically complete selectivity to naphthyl-methyl-urethane.

EXAMPLE 2

At 150° C. and 100 mm Hg, 14 g of beta-naphthol and 9 g of dimethyl urethane were reacted in the presence of 0.7 g $ZnCl_2$. A conversion of 2% of naphthol to methyl naphthyl urethane was obtained.

EXAMPLE 3

At 170° C. and 100 mm Hg, 14 g of alpha-naphthol and 18 g of dimethyl urethane were reacted in the presence of 1.5 g of titanium tetra-isopropylate. In 5 hours a 32% convertion of naphthol was obtained, with total selectivity to methyl naphthyl urethane.

What we claim is:

1. The process of preparing an aromatic urethane having the formula:

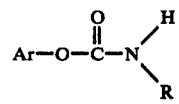

wherein Ar is a phenyl or naphthyl group and R is alkyl, which consists in reacting the corresponding alkyl carbamate ester with a phenol or naphthol corresponding to Ar, in the liquid phase and in the presence of a catalyst consisting of $AlCl_3$ or $ZnCl_2$ under subatmospheric conditions in the temperature range of 100° to 300° C.

2. A process for the preparation of an aromatic urethane as claimed in claim 1, wherein the reaction is effected in the temperature range between 150° and 250° C.

3. A process for the preparation of an aromatic urethane as claimed in claim 1, wherein the reaction is effected at a phenol or naphthol/alkyl carbamate ester molar ratio between 10:1 and 1:10.

4. A process for the preparation of naphthyl methylcarbamate, which consists in reacting alpha-naphthol or betanaphthol and methyl methylcarbamate in the presence of a catalyst consisting of $AlCl_3$ or $ZnCl_2$ under subatmospheric conditions at a temperature in the range of 150° to 170° C.

* * * * *